United States Patent
Maletz et al.

(10) Patent No.: US 8,501,834 B2
(45) Date of Patent: Aug. 6, 2013

(54) DUAL-CURING, MULTI-COMPONENT DENTAL COMPOSITION

(75) Inventors: Reinhard Maletz, Cuxhaven (DE); Wigand Krumme, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 171 days.

(21) Appl. No.: 13/085,034

(22) Filed: Apr. 12, 2011

(65) Prior Publication Data

US 2011/0250558 A1    Oct. 13, 2011

(30) Foreign Application Priority Data

Apr. 12, 2010 (DE) .......................... 10 2010 003 884

(51) Int. Cl.
*A61F 2/00* (2006.01)

(52) U.S. Cl.
USPC .................. 523/115; 522/47; 522/9; 522/13; 522/24; 522/30; 526/328.5; 523/116; 604/187; 604/191

(58) Field of Classification Search
USPC ................ 523/116; 522/47; 526/328.5
See application file for complete search history.

(56) References Cited

U.S. PATENT DOCUMENTS

| | | | |
|---|---|---|---|
| 4,369,296 A | | 1/1983 | Podszun et al. |
| 4,490,497 A * | | 12/1984 | Evrard et al. ............... 523/116 |
| 4,507,444 A | | 3/1985 | Slawyk et al. |
| 5,750,590 A | | 5/1998 | Schaefer et al. |
| 6,063,831 A | | 5/2000 | Kubo et al. |
| 6,305,936 B1 | | 10/2001 | Jensen et al. |
| 6,387,981 B1 * | | 5/2002 | Zhang et al. ............... 523/117 |
| 6,709,271 B2 | | 3/2004 | Yin et al. |
| 6,800,671 B1 | | 10/2004 | Montgomery et al. |
| 2002/0146662 A1 * | | 10/2002 | Radl et al. ............... 433/90 |
| 2007/0142495 A1 * | | 6/2007 | Neffgen et al. ............ 523/116 |
| 2010/0016466 A1 | | 1/2010 | Lueck |
| 2010/0152296 A1 | | 6/2010 | Marmarinos et al. |
| 2010/0292363 A1 | | 11/2010 | Neffgen et al. |

FOREIGN PATENT DOCUMENTS

| | | |
|---|---|---|
| DE | 1795395 A1 | 1/1972 |
| DE | 4233886 C1 | 3/1994 |
| DE | 19905093 A1 | 8/2000 |
| DE | 102008028306 A1 | 2/2009 |
| EP | 2070506 A1 | 6/2009 |

* cited by examiner

*Primary Examiner* — David Buttner
*Assistant Examiner* — Peter A Salamon
(74) *Attorney, Agent, or Firm* — Duane Morris LLP; J. Rodman Steele, Jr.; Greogory M. Lefkowitz

(57) ABSTRACT

A dual-curing, multi-component dental composition is described. The dental composition can include:
(a) one or more photopolymerizable monomers selected from the group consisting of acrylates and methacrylates;
(b) one or more photoinitiators, selected from the group consisting of alpha-diketones, benzoin alkyl ethers, thioxanthones, benzophenones, acylphosphinoxides, acetophenones, ketals, titanocenes, borates and sensitizing colorants;
(c) one or more molecular weight regulators selected from the group consisting of compounds which can be converted with a radical of a monomer of component (a), wherein the conversion takes place by abstraction of an H-radical from the molecular weight regulator in the allyl position;
(d) one or more polymerization inhibitors for increasing the storage stability of the composition;
(e) one or more inorganic fillers;
(f) one or more initiators for a chemical curing at ambient temperature, and if necessary one or more further additives. Related methods and uses are also described.

23 Claims, 1 Drawing Sheet

DUAL-CURING, MULTI-COMPONENT DENTAL COMPOSITION

CROSS-REFERENCE TO RELATED APPLICATIONS

This application claims priority to German Patent Application No. 10 2010 003 884.9, filed Apr. 12, 2010, the entire contents of which are incorporated herein by reference.

FIELD OF THE INVENTION

The present invention concerns a dual-curing, multi-component dental composition containing one or more specific additives (molecular weight regulators), a corresponding method for producing such a composition and the use of specific molecular weight regulators for producing a dual-curing, multi-component dental composition.

BACKGROUND OF THE INVENTION

Photocurable composite materials are the most commonly used dental materials. Modern dental composites are usually a combination of an organic plastic matrix and inorganic fillers, wherein the inorganic phase and the organic phase are bonded together. The composition, which has not yet been cross-linked, thus contains free monomers or monomer mixtures, inorganic fillers or filler mixtures, initiators and in most cases colorants.

The curing of photocurable dental composite materials takes place by means of photoinitiated polymerization. As a result of this, following photochemical activation of an initiator system, chain reactions are started, wherein by means of three-dimensional cross-linking the liquid monomers are converted to a solid polymerizate.

The provision of prepared teeth with temporary prostheses, for example in crown and bridge prosthetics, is of particular importance to patients since these ensure the correct aesthetics, phonetics and occlusion. They also protect the hard dental material from caries and fractures and the pulp from trauma or injury. They also safeguard the dentine wound of the drilled tooth against thermal, chemical, mechanical and bacteriological stimuli, which within a very short time can lead to inflammatory processes in the pulp.

Various methods can be used in the production of temporary prostheses.

In the direct method, for example, prior to preparation with alginate or a silicon mass, a local impression is taken. Following preparation the plastic composition is introduced into the impression and placed again into the mouth of the patient.

Alternatively prefabricated plastic sleeves can also be used for example, wherein the temporary prosthetic is created without first taking an impression. The sleeves are individually tailored to the mouth by cutting and milling, filled with a self-polymerizing plastic and then placed on the prepared tooth.

Materials for the production of temporary crowns and bridges must guarantee the functioning of the prostheses for the time that they are present in the mouth. To this end the materials must meet a number of requirements.

Thus the materials must not release any toxic substances while in use. Harmful substances may be given off in the oral cavity through diffusion, friction, deterioration and by dental treatments such as grinding. Release of plastic monomers especially must be prevented as these are potential allergens and can leak into the oral cavity by diffusion in the form of unconverted residual monomers.

Furthermore, the material should have good mechanical properties, in particular in terms of hardness, strength, modulus of elasticity and abrasion behavior in order that, together with an optimum adaptation to the occlusal conditions, trouble-free functioning for the time in situ is ensured.

The surface of the temporary prosthesis should be smooth and able to be polished to a high gloss. The smoothness of the material serves to prevent the deposits of plaque while the high-gloss polishing capability seeks to meet aesthetic needs. A rough surface could also lead to irritation of the tongue and trigger paresthesia.

The temporary prosthesis, together with the securing material, should also exhibit a high level of tightness at its edges, in order to prevent the infiltration of bacteria and substances.

Furthermore, during the intra-oral phase of polymerization, the material should not cause any heat damage. The thermal energy released during cross-linking should not cause any pain in the mouth of the patient. At the same time the material should provide a complete and sealed covering of the ground tooth surface thereby protecting the tooth from thermal and mechanical irritation.

The crown and bridge materials used nowadays have a plastic base and are quite different in their chemical make-up. As a rule they contain methacrylates, acrylates and catalysts, inhibitors, cross-linking agents, plasticizers, accelerators, UV absorbers, fillers and so on. The curing of these products takes place either chemically through autopolymerization following the mixing of two pastes, the so-called base paste with the so-called catalyst paste in the static mixing tube of a double-chamber cartridge, or by dual-cured, i.e. both chemically and by means of irradiation at a suitable wavelength.

One distinct disadvantage of an autopolymerizable plastic composition is the heat developed during the exothermic polymerization which represents a danger to the pulp.

The quantity of heat released is dependent upon the dosing of the catalyst system used, the molding mass (impression substance) and the quantity processed. In the literature a number of working groups have measured differing temperature peaks for temporary crown and bridge materials which depending on the test set-up and the chemical composition vary between 25 and 94° C. Apart from the maximum temperature of the polymerization process the way in which the temperature develops is important. Thus for example the temperature development of the curing of a composition of a temporary crown and bridge material in a temperature-time diagram at the start of cross-linking appears relatively flat and then, around the point in time of the temperature maximum, briefly and suddenly increases and gives off a lot of heat within a very short space of time. On the other hand such a curve can also take a form in which a relatively long-lasting, but weaker, development of heat takes place.

Self-curing temporary crown and bridge materials are normally first applied in the impression mold. Here the usually two-component composition is pushed through a static mixing tube of a double chamber cartridge. During this process the components are mixed together and thus made to react. The impression mold filled with the mixed material is then inserted in the mouth and pushed on to the prepared stump. Once the radically curable plastic material in the impression mold has passed through its elastic phase it is removed from the stump after approximately 1 minute and taken out of the mouth where it finally cures extra-orally. Here the thermosetting also reaches its maximum temperature.

As early as during the elastic phase, where the maximum temperature has not yet been reached, a state of the dental composition is very quickly reached in which it starts to gel and the external shape essentially no longer changes. The viscosity of the composition is now so high that for the still un-reacted, unsaturated groups it becomes increasingly harder to obtain sufficient mobility to find a conversion partner. As a rule free monomers remain in the network and could subsequently be given off into the surroundings in the mouth.

A further disadvantage is the change in density in the material that occurs during cross-linking, which in the worst case scenario can lead to a change in the external form. If crown and bridge materials cure without keeping their shape, then this can later lead to a poor fit. The crown then no longer covers the stump completely. At these points microorganisms could later infiltrate and attack the tooth stump from the inside. This change in density is referred to as shrinkage or volume reduction of the reaction resin mass. This is primarily dependent upon the number of functional groups that have reacted. The shrinkage takes place both in the fluid state, thus at the very start of the polymerization, as well as during and after gelling. Overall shrinkage is subdivided into a physical and chemical component. Whereas physical shrinkage is directionally determined and runs spatially, from the outer areas of the polymerizate, operates in a similar fashion to and, in accordance with the drop in temperature that takes place, towards the central point of the molding material as it cures, the chemical component is not directionally determined, takes place solely as a result of the polymer formation and is highly dependent upon the geometrical conformation and configuration parameters of the newly constructed macromolecule.

With photocurable materials similar problems can arise. It has been found that a lower release of heat and lower shrinkage forces arise if the start of polymerization can be delayed from the outset. Such polymerization behavior can be achieved if, by having lower light power at the start and subsequently raising the light power to a maximum value, the polymerization is deliberately delayed. As a result of the lower light power at the start of curing the material remains flowable for longer, the gelling point is reached later, and the mobility of the functional groups is retained for longer so that higher conversion rates are achieved. The method used here is referred to as soft-start-polymerization. Together with the so-called "incremental method", in which thin layers are individually photocured (very time-consuming), it is a further method that allows a reduction of high heat peaks and the shrinkage associated with the release of heat.

Approaches for providing low shrinkage dental materials, such as the use of ring opening metathesis polymerization (ROMP) curing, byciclic monomers (DE 199 05 093 A1);

the addition of certain additives (cumarone resin, polyvinyl acetate, alcohol surfactants) prior to curing of the composition (DE 198 51 038 A1);

the use of cationic polymerizable oxetanes (U.S. Pat. No. 5,750,590);

the use of epoxy resins, containing nanoscale inorganic oxides and the combination of different sized fillers (U.S. Pat. No. 6,709,271 B1)

have thus far not been able to establish themselves in practice.

For self-polymerizing and, to a much larger extent, for dual-curing dental compositions factors such as the release of heat and shrinkage represent problems that are currently countered primarily by the method and less so by the chemical formulation of the dental composition.

In EP 1 720 506, WO 2009/083168 A1, DE 10 2008 028 306 A1, EP 1 872 767 A1 and EP 2 070 506 various polymerizable dental materials are described. The dental materials disclosed there can be cured thermally, chemically, photochemically and/or though a reaction with the moisture in the mouth or air. Alongside many other stabilizers, these documents disclose, amongst others, in the respective lists of stabilizers terpinenes. A combination of photopolymerizable monomers and terpinenes is not disclosed in said documents.

In another area of application in dentistry, namely dental coatings, in systems for radical polymerization of photocurable masses the problem of high heat generation has in many cases been tackled either by adding non-reactive organic admixtures to the composition and/or using monomers with a high molecular weight, i.e. compounds with a low proportion of double bonds. In this connection U.S. Pat. No. 6,305,936 B1, U.S. Pat. No. 6,800,671 B1 and WO 2008/096182 are cited.

DE 42 33 886 C1 discloses polymerizable conditioning agents based on methacrylate and a method for pre-treating the surface of shaped bodies made from polyacrylate, polymethacrylate and polycarbonate plastics prior to application of polymerizable methacrylate material and use of the conditioning agent. The conditioning agent may contain monocyclic terpene hydrocarbon. Intra-oral use appears excluded due to the use of alkyl monomethacrylates, which should be categorized as posing a toxicological risk.

DE 27 27 480 A1 discloses impact-resistant, vitreous plastic alloys of polymethacrylates and aliphatic polyurethane ureas. Methods for the production thereof are disclosed, in which use is made of monomer mixtures comprising sulfur-containing molecular weight regulators. Not disclosed are compositions for the dental field.

DE 17 95 395 A discloses methods for producing polymers and copolymers of (meth)acrylic acid esters and acrylonitrile in the presence of polymerization catalysts and compounds having a six-membered ring containing two non-conjugated double bonds, one of which may be semicyclic (exocyclic). The specifically disclosed polymerization catalysts are thermal catalysts. Photoinitiators or photopolymerizable dental compositions are not disclosed.

U.S. Pat. No. 4,490,497 A discloses powder/liquid systems for a surgical cement, which can be used in the extra-oral production of dental prostheses. A liquid component of the composition comprises as the "chain stopper" for example a diunsaturated monocyclic terpene or a monounsaturated bicyclic terpene. Not disclosed are dual-curing compositions, in particular dual-curing dental compositions which are suitable for direct use in the oral cavity. Furthermore, the powder/liquid systems described are not suitable for distribution by means of dental syringes. The systems described in U.S. Pat. No. 4,490,497 A also have very long setting times. A link between the use of "chain stoppers" and polymerization stabilizers (such as alkyl-substituted monophenols) is not disclosed.

DE 30 10 373 A1 discloses methods for polymerizing methacrylic acid methyl esters or mixtures thereof with further vinyl monomers in the presence of enol ethers. The polymers produced by the disclosed method are referred to as being particularly suitable for use in the dental field, for example for producing prostheses according to the powder/liquid method; not disclosed, however, are dual-curing, multi-component compositions.

EP 1 720 506 B1 discloses a filled and polymerizable dental material and also a method for the production thereof. As use examples, the following are mentioned: tooth filling materials, stump build-up materials, materials for temporary crowns and bridges, dental cements, adhesives, materials for artificial teeth, veneering materials, sealing materials and dental varnish. It is disclosed that the dental material may contain additives and/or modifiers in order to set certain properties; a long list of examples includes "terpinenes". Not disclosed, however, are dual-curing, multi-component compositions, which comprise a molecular weight regulator.

The person skilled in the art, e.g. the dentist, wants an extra-oral working time that is (as) long (as possible) and then an intra-oral setting time that is as short as possible after introduction into the mouth (i.e. generally at a slightly increased temperature). In this situation, the curing may not be accompanied by a large exotherm, since at high temperatures living tooth structure can suffer long-term damage.

In order to influence working time and setting time, a dental composition can be varied. For example, if in an otherwise identical composition the quantity added of a polymerization inhibitor in a radically polymerizable composition is increased, both the working time and the setting time increase steadily, wherein the delay in hardening is approximately proportional to the quantity added of polymerization inhibitor.

The object of the invention was to provide dental dual-curing (using dental chemistry with simultaneous photo-curing) compositions, which compared with the compositions of the prior art have a lower heat development and a lower shrinkage.

A specific dental task was to prepare a filled, dual-curing dental composition (in particular a composite material, which can be used as a dental filling material, as a flowable composite material, as a crown material, as a bridge material and/or as a stump build-up material), which should be able to be applied with a dental syringe and which should preferably be present in the form of two pastes, i.e. in the form of a paste/paste system.

Furthermore, the working time should be sufficiently long and at the same time the setting time should be as short as possible. Here, despite the shortest possible setting time, a temperature development that is as small as possible should take place, i.e. an acceptable temperature maximum during the curing of the dental composition in the oral cavity should not be exceeded.

The present invention concerns a dual-curing, multi-component dental composition comprising:
(a) one or more photopolymerizable monomers selected from the group consisting of acrylates and methacrylates, preferably from the group of methacrylates;
(b) one or more photoinitiators, selected from the group consisting of alpha-diketones, benzoin alkyl ethers, thioxanthones, benzophenones, acylphosphinoxides, acetophenones, ketals, titanocenes, borates and sensitizing colorants;
(c) one or more molecular weight regulators selected from the group consisting of compounds which can be converted with a radical of a monomer of component (a), wherein the conversion takes place by abstraction of an H-radical from the molecular weight regulator in the allyl position;
(d) one or more polymerization inhibitors for increasing the storage stability of the composition, preferably selected from the group consisting of hydroquinone monomethyl ether (HQME), phenols, preferably 2,6-di-tert.-butyl-4-methylphenol (BHT) and tert.-butylhydroxyanisol (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof;
(e) one or more inorganic fillers;
(f) one or more initiators for a chemical curing at ambient temperature (preferably 23° C.), preferably a redox initiator system,
and if necessary one or more further additives.

Surprisingly it has been found that dental compositions with a base of photopolymerizable monomers from the group of acrylates and methacrylates in the form of dual-curing, multi-component dental compositions according to the invention can be provided, which do not give off large quantities of heat into the surroundings, have low physical shrinkage and high cross-linking rates, and which following curing of the material no longer contain any harmful quantities of un-converted monomers which might subsequently have an adverse effect on the tissue.

Surprisingly it has also been found that a combination of one or more molecular weight regulators of component (c) and one or more polymerization inhibitors of component (d) in the dual-curing dental compositions according to the invention leads to such a curing behavior and such a polymerization kinetics relationship that after the mixing (e.g. in a static mixing tube) a long period of extra-oral working of the dental material is possible (cf. the remarks on the working time further below); however after intra-oral application, a rapid curing and setting takes place (cf. the remarks on the setting time further below).

Since the compositions according to the invention are dual-curing, the polymerization or the curing is normally accelerated further by exposure to light.

To summarize briefly, through the compositions according to the invention, in particular in one of the embodiments identified below as being preferred or particularly preferred, a comparatively long working time can thus be achieved within a certain context, without the setting time thereby also being extended.

The terms and definitions of "working time" and "setting time" and the methods for their determination relate within the context of the present text to DIN EN ISO 4049 (as at: March 2010).

The working times and setting times for different dual-curing, two-component dental compositions according to the invention containing 0.02 wt. % of the polymerization inhibitor BHT (2,6-di-tert.butyl-4-methylphenol; compound of component (d)) and different quantities of γ-terpinene (compound of component (c)) (in an otherwise identical composition) are illustrated in FIG. 1.

The working times and setting times for different dual-curing, two-component dental compositions not according to the invention containing different quantities of the polymerization inhibitor BHT (in an otherwise identical composition) in the absence of a molecular weight regulator according to component (c) are illustrated in FIG. 2.

According to the method of DIN EN ISO 4049, the working time is determined at a (forming) temperature of 23° C. and the setting time at 37° C. These (forming) temperatures correspond to normal extra-oral and intra-oral conditions.

DETAILED DESCRIPTION

Figure 1:
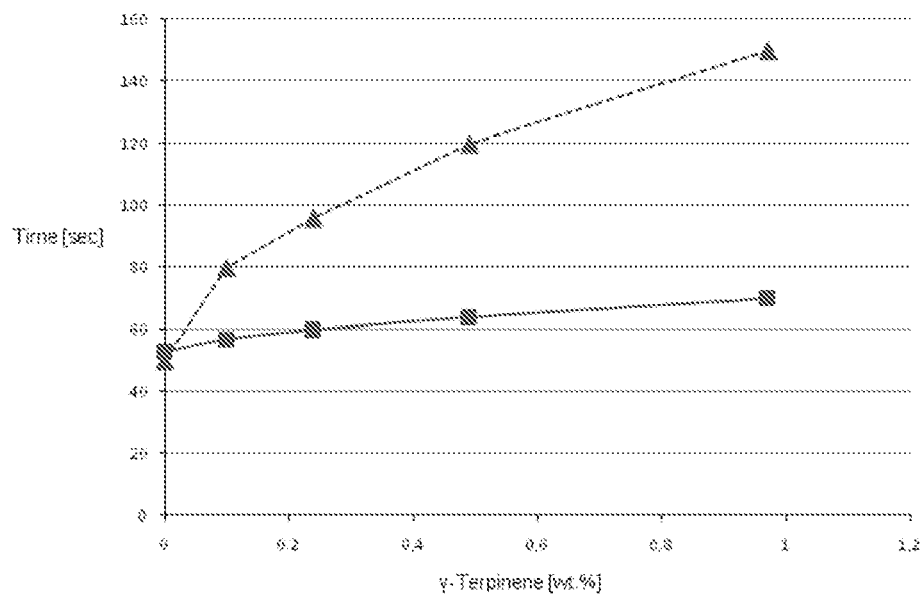
FIG. 1 illustrates the working times and setting times for a constant quantity of BHT as a function of the content of γ-terpinene of an otherwise identical dental composition according to the invention. The x-axis of FIG. 1 indicates the percentage of γ-terpinene in the respective composition, the y-axis the time in seconds. The working times given correspond to the dashed line with triangles, the setting times given to the solid line with squares.

From FIG. 1 it can directly be seen that the setting time deviates increasingly from the working time as the content of γ-terpinene rises, i.e. there is, so to speak, an uncoupling of setting time and working time.

Figure 2:
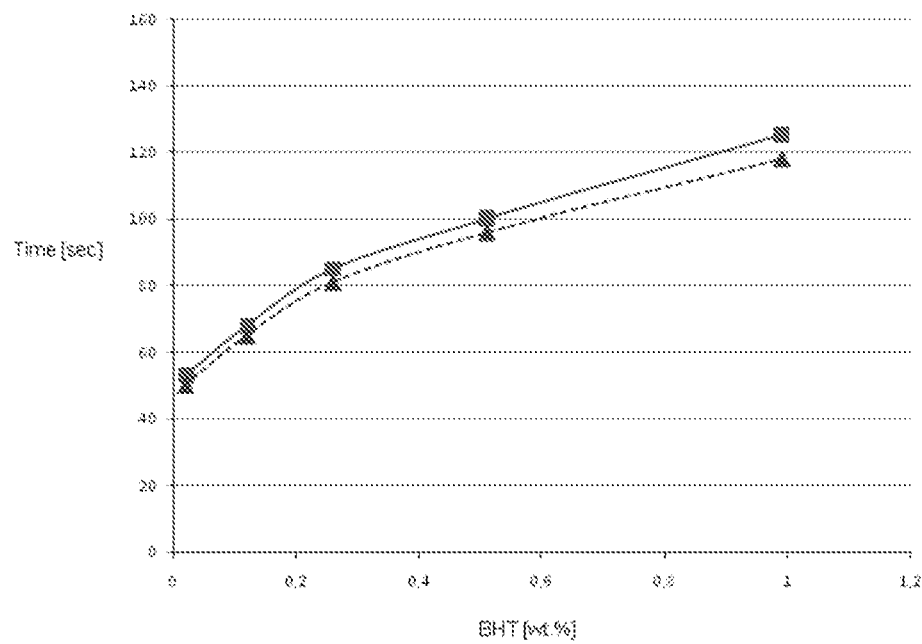
FIG. 2 illustrates in an exemplary fashion the working times and setting times as a function of the content of BHT in an otherwise identical composition. The x-axis of FIG. 2 indicates the percentage of BHT in the respective composition, the y-axis the time in seconds. The working times given correspond to the dashed lower line with triangles, the setting times given to the solid upper line with squares.

From FIG. 2, on the other hand, it can directly be seen that the curve of the setting time values corresponds qualitatively to that of the working time values and—in the thoroughly analyzed examples—the setting time is slightly longer in each case than the corresponding working time.

The results represented in FIGS. 1 and 2 result from our own experiments with compositions corresponding to or based on the formulation of the reference example and the formulations of the examples according to the invention Exp. 1 to Exp. 4. More precise details on this can be found further below (see also the subsequent tables 1, 1A-1, 1A-2 and 1B).

A preferred dental composition according to the invention has a setting time (according to DIN EN ISO 4049, as specified above) of at most 10 minutes, preferably of at most 6 minutes, further preferably of at most 3 minutes.

A preferred dental composition according to the invention is two-component, and is preferably present in the form of two pastes.

Dual-curing compositions according to the invention are generally present in the form of a base paste and a catalyst paste. A preferred dental composition according to the invention is two-component and is present in the form of a base paste and a catalyst paste, wherein preferably the mixing ratios, based on weight, of base paste to catalyst paste are in the range 1:2 to 10:1, more preferably in the range 1:1 to 10:1.

In a preferred embodiment, component (d) is partially or fully contained in the catalyst paste of a dental composition according to the invention.

A preferred dental composition according to the invention can be distributed and applied with a dental syringe, in particular with a double syringe or double-chamber cartridge, via a cannula, preferably a static mixing tube.

Double-chamber syringes and double-chamber cartridges with mixing attachment are preferred here, because with these a quick and bubble-free mixing in precisely defined mixing ratios is possible.

A preferred dental composition according to the invention, upon application in the mouth, has a flow behavior and a stability such that no running or spreading of the applied dental composition takes place.

Preferably the viscosity of at least one component, more preferably, however, the viscosity of each component of the dental composition according to the invention is greater than or equal to 10 Pas and is preferably in the range 10 Pas-190 Pas, particularly preferably in the range 20-140 Pas.

In the case of higher viscosity values, in particular above 190 Pas, the flow behavior of the composition is significantly worse and can only be pressed out of a normal dental mixing tip with great difficulty.

Dental compositions with a viscosity in the very particularly preferred range of 20-140 Pas can be applied in the oral cavity using normal dental mixing tips in a particularly convenient manner and in a way that is agreeable both for the patient and for the treating dentist, without undesired droplet formation and without the compositions flowing away.

The viscosities given here refer to the measurement at 23° C. with a plate/plate rheometer (diameter of the plate: 25 mm) with a shear rate of 10/sec. at a gap width of 1 mm.

Likewise preferred according to the invention is a dental composition in which component (f) comprises:

(f-a)
one or more initiators, selected from the group consisting of inorganic peroxides, organic peroxides, inorganic hydroperoxides, organic hydroperoxides, barbituric acid derivatives, malonyl sulfamides, protonic acids, Lewis or Broensted acids, compounds releasing such acids and carbenium ion donors such as preferably methyl triflate or triethyl perchlorate;

one or more co-initiators selected from the group consisting of tertiary amines, heavy metal compounds, in particular compounds from groups 8 and 9 of the periodic table ("iron and copper group"), compounds with ionically bonded halogens or pseudohalogens, preferably quaternary ammonium halides, and weak Broenstedt acids, such as for example alcohols and water, and/or (f-b) a redox initiator system, comprising (f-b1) barbituric acid, thiobarbituric acid, a barbituric acid and/or a thiobarbituric acid derivative, (f-b2) if necessary a peroxodisulfate- and/or a peroxodiphosphate compound, (f-b3) a copper compound, (f-b4) a compound with an ionically present halogen atom, wherein the initiators of component (f) are distributed over separate components of the dental composition so that a chemical initiation is triggered through the mixing of said components.

Various initiator systems for chemical curing and corresponding redox initiator systems will be known to a person skilled in the art. In this connection, by way of example, reference is made to EP 1 720 506 and especially EP 1 839 640 and the documents cited therein.

Molecular weight regulators (also referred to in the following simply as regulators) are in themselves known and commercially available. They are used, for example, in the solution polymerization of olefins, in the emulsion polymerization of methacrylates or in the production of molded bodies from polymethylmethacrylate (PMMA) molding masses by compression molding or injection molding.

Molecular weight regulators constitute so-called transfer reagents, which in a free radical reaction undergo transfer reactions involving mechanical H-abstraction and transfer of the radical function to the regulator. As a result of their function the regulators then reappear in the form of end groups in the cross-linked polymerizate.

Normal regulators are by way of example aldehydes and ketones, such as formaldehyde, acetaldehyde, propionaldehyde, n-butyraldehyde, isobutyraldehyde, methylethylketone, acetone, methylisobutylketone, formic acid, ammonium formiate, hydroxylammonium sulfate and hydroxylammonium phosphate, compounds containing sulfur in organically bonded form, such as di-n-butyl sulfide, di-n-octyl sulfide, diphenyl sulfide, diisopropyl disulfide, di-n-butyl disulfide, di-n-hexyl disulfide, diacetyl disulfide and di-tert.-butyl trisulfide, compounds containing sulfur in the form of SH groups, such as n-butyl mercaptan, n-hexyl mercaptan and n-dodecyl mercaptan, octadecyl mercaptan, other sulfurous compounds such as hydrogen sulfites, disulfites, compounds such as mercaptoethanol, mercaptobutanol, mercaptoacetic acid, 3-mercaptopropionic acid, mercaptosuccinic acid, thioglycerin, thioglycolic acid, diethanol sulfide, thiodiglycol, ethylthioethanol, 2,2,4,6,6-pentamethylheptan-4-thiol, 2,2,4,6,6,8,8-heptamethylnonan-4-thiol, thiourea, dimethyl sulfoxide, ethylhexylthioglycolate, pentaerythritol tetrathioglycolate, mercaptopropyltrimethoxysilane, or allyl compounds such as allyl alcohol, allyl bromide, or benzyl compounds such as benzyl chloride or alkyl halogenides such as chloroform, bromotrichloromethane or tetrachloromethane, tetrabromomethane, methylene chloride, further lower and higher molecular monovalent or multivalent alcohols such as methanol, ethanol, n-propanol, isopropanol, tert.-butanol, sec-butanol, n-butanol, amyl alcohol, cyclohexanol, octanol, dodecanol, 1-ethyl hexanol, glycerin, stearyl alcohol, oleyl alcohol, hydroxyethyl methacrylate or amines such as triethylamine and toluene or ethyl benzene.

The abovementioned regulators are unsuitable for the use envisaged here, however. Thus sulfurous molecular weight regulators have an intense and typically unpleasant smell, which rules out their use as a component of a dental material. Dental compositions according to the invention therefore preferably do not comprise any sulfurous molecular weight regulators. It has also been found that lower or higher molecular, mono- or polyvalent alcohols do not bring about any regulatory effect and remain ineffective. The same applies to aldehydes and ketones.

The precise reason for the success according to the invention, when using the abovementioned molecular weight regulators (c), is not known in detail. Presumably, however, there is a special and previously unexpected interaction between the monomer(s) and the molecular weight regulator(s), allowing during the photopolymerization of the composition according to the invention the molecular weight regulators (c) in some way and to some extent to influence the conduct of the polymerization so that the chain length, cross-linking and residual monomer content of the polymer that forms are fashioned such that the desired characteristics are obtained.

Molecular weight regulators that are suitable according to the invention are for example various terpinenes ($\alpha$-terpinene, $\beta$-terpinene, $\gamma$-terpinene), phellandrenes ($\alpha$-phellandrene, $\beta$-phellandrene) and terpinolene (also known as $\delta$-terpinene), 1,4-cyclohexadiene (substituted if necessary), 1,3-cyclohexadiene (substituted if necessary), 1,4-dihydronaphthalene, 1,4,5,8-tetrahydronaphthalene, 2,5-dihydrofuran or dimeric $\alpha$-styrene (2,4-diphenyl-4-methyl-1-pentene) and linoleic acid and $\alpha$-linolenic acid.

Molecular weight regulators to be used by preference according to the invention as component (c) of a composition according to the invention are compounds with two or more double bonds, preferably compounds with two or more double bonds which through abstraction of an allyl H-atom can form a delocalized electron system, extending across 5 or more C-atoms, preferably dienes which through abstraction of an allyl H-atom can form a delocalized electron system, extending across 5 C-atoms.

Molecular weight regulators to be used by preference according to the invention as component (c) of a composition according to the invention are selected from the group of monoterpenes, preferably from the group comprising monoterpene dienes, more preferably from the group consisting of $\alpha$-terpinene, $\beta$-terpinene, $\gamma$-terpinene, $\alpha$-phellandrene, $\beta$-phellandrene and terpinolene or are selected from the group consisting of linoleic acid, linolenic acid and other substituted or non-substituted cyclohexadienes.

Particularly preferred regulators according to the invention are $\alpha$-terpinene and $\gamma$-terpinene, with particular preference for $\gamma$-terpinene. The best results in the context of the present invention were obtained with these molecular weight regulators.

In a composition according to the invention, mixtures of molecular weight regulators can of course also be used.

Preferred dental compositions according to the invention comprise
component (a) in a quantity of 19-70 wt. %, preferably in a quantity of 30-65 wt. %;
component (c) in a quantity of 0.05-5.00 wt. %, preferably 0.1-2.0 wt. %, more preferably 0.1-0.5 wt. %, and
component (e) in a quantity of 25-80 wt. %, preferably 30-65 wt. %,
in each case in relation to the total mass of the dental composition.

Dental compositions preferred according to the invention comprise
components (b) and (f) in a total quantity in the range 0.25-3 wt. %, preferably in a total quantity in the range 0.35-1.5 wt. %, in relation to the total mass of the dental composition.

Dental compositions preferred according to the invention comprise
component (e) in a quantity of at least 10 wt. %, preferably at least 20 wt. %, more preferably at least 25 wt. % and preferably at the same time
components (b) and (f) in a total quantity in the range 0.25-3 wt. %, preferably in a total quantity in the range 0.35-1.5 wt. %, and/or preferably at the same time
component (d) in a quantity of 0.005-0.100 wt. %, preferably 0.005-0.075 wt. %, more preferably 0.010-0.050 wt. %,
in each case in relation to the total mass of the dental composition.

Dental compositions further preferred according to the invention comprise
component (a) in a quantity of 19-70 wt. %, preferably in a quantity of 30-65 wt. %,
component (c) in a quantity of 0.05-5.00 wt. %, preferably 0.1-2.0 wt. %, more preferably 0.1-0.5 wt. %;
component (e) in a quantity of 25-80 wt. %, preferably 30-65 wt. %, and
components (b) and (f) in a total quantity in the range 0.25-3 wt. %, preferably in a total quantity in the range 0.35-1.5 wt. %,
in each case in relation to the total mass of the dental composition.

Dental compositions further preferred according to the invention comprise
component (a) in a quantity of 19-70 wt. %, preferably in a quantity of 30-65 wt. %,
component (b) in a quantity of 0.05-1.00 wt. %, preferably 0.05-0.5 wt. %, more preferably 0.05-0.2 wt. %;
component (c) in a quantity of 0.05-5.00 wt. %, preferably 0.1-2.0 wt. %, more preferably 0.1-0.5 wt. %;
component (e) in a quantity of 25-80 wt. %, preferably 30-65 wt. %, and
component (f) in a quantity of 0.2-2 wt. %, preferably of 0.3-1.0 wt. %,
in each case in relation to the total mass of the dental composition.

For the purposes of this text the "total mass of the dental composition" in a multi-component system refers to the total mass of all components of the dental composition.

A preferred dental composition according to the invention, as well as one or more photoinitiators of component (b), additionally contains one or more initiators different from component (b) for a chemical curing at ambient temperature (preferably 23° C.) of component (f).

Component (a)—Photopolymerizable Monomers

The radically photopolymerizable monomers can be substances containing at least two ethylenic groups such as for example, but without be restricted to, the (meth)acrylate monomers normally used in composite materials in dental chemistry.

In a number of compositions according to the invention, preferably the presence of methyl methacrylate is dispensed with, since methyl methacrylate is assessed as posing a toxicological risk. A dental composition according to the invention therefore preferably contains at most 5 wt. % methyl methacrylate, more preferably at most 2 wt. %, further preferably at most 1 wt. %, particularly preferably at most 0.5 wt. %, in each case in relation to the total weight of the composition. In a further preferred embodiment, a dental composition according to the invention is free from methyl methacrylate.

In a preferred embodiment, component (a) of a dental composition according to the invention contains no alkyl monomethacrylates. In a further preferred embodiment, a dental composition according to the invention contains at most 5 wt. % alkyl monomethacrylates, preferably at most 2 wt. %, more preferably at most 1 wt. %, further preferably at most 0.5 wt. %. Particularly preferred is a dental composition according to the invention that is free from alkyl monomethacrylates.

The patent literature mentions a number of other compounds (for example also in DE 39 41 629 A1, which by way of reference is a component part of this application), which are all diesters of acrylic or methacrylic acid and are suitable for use in a composition according to the invention.

In a preferred dental composition according to the invention, component (a) contains one or more dimethacrylate monomers selected from the group consisting of ethylene glycol dimethacrylate (EGDMA), 1,6-hexandiol dimethacrylate (HEDMA), triethylene glycol dimethacrylate (TEGDMA), 1,12-dodecandiol dimethacrylate (DODMA), ethoxylated bisphenol A dimethacrylate, polyethylene glycol dimethacrylate (PEGDMA), 7,7,9-trimethyl-4,13-dioxo-5,12-diazahexadecan-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol-dimethacrylate, glycerin dimethacrylate, bisphenol A glycidyl methacrylate (bis-GMA) and dimethacrylates of dihydroxymethyltricyclo[5.2.1.0$^{2,6}$]decane.

Express preference is also for the corresponding dimethacrylates or diacrylates of dihydroxymethyltricyclo [5.2.1.0$^{2,6}$]decane, as described in printed publications DE 1816823, DE 2419887, DE 2406557, DE 2931926, DE 3522005, DE 3522006, DE 3703120, DE 102005021332, DE 102005053775, DE 102006060983, DE 69935794 and DE 102007034457, which by way of reference are a component part of this application.

The radically photopolymerizable monomers can also be hydroxyl compounds with at least one ethylenic double bond. Here all hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol-dimethacrylate, glycerin dimethacrylate, 2,2-bis[4-[3-methacryloyloxy-2-hydroxypropoxy]phenyl]propane.

In a further preferred embodiment, component (a) of a dental composition according to the invention consists of monomers selected from the group consisting of (meth)acrylate monomers with at least two ethylenic groups and hydroxyl compounds of acrylates or methacrylates, or component (a) comprises such monomers.

In a further preferred embodiment, component (a) of a dental composition according to the invention consists of monomers selected from the group consisting of methacrylate monomers with at least two ethylenic groups and hydroxyl compounds of methacrylates, or component (a) comprises such monomers.

Further, so-called ormocers, which will be known to persons skilled in the art and which are for example described in DE 199 03 177 or in DE 44 16 857, which by way of reference are a component part of this application, can be used.

A composition according to the invention can further contain one or more acid group-containing photocurable substances. Acid group-containing monomers can in particular have a carboxylic acid, a phosphoric acid, a phosphonic acid, a sulfonic acid and/or a thiophosphoric acid function.

The acid group-containing, photocurable compound can be a polymerizable monomer containing one or more acid functions in a molecule.

Suitable monomers containing a phosphoric acid group are, for example, 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)-acryloyloxyhexyl dihydrogen phosphate, 10-(meth)acryloyloxydecyl dihydrogen phosphate (MDP), 6-(meth)-acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis[5-(2-(meth)acryloyloxyethoxycarbonyl)heptyl]hydrogen phosphate.

Suitable monomers containing a carboxylic acid group are for example, 4-(meth)acryloxyethyl trimellitic acid (4-MET), 4-(meth)acryloxyethyl trimellitic acid anhydride (4-META), 4-(meth)acryloxydecyl trimellitic acid, 4-(meth)acryloxydecyl trimellitic acid anhydride, 11-(meth)acryloyloxy-1,1-undecane dicarboxylic acid, 1,4-di(meth)acryloyloxy pyromellitic acid, 2-(meth)acryloyloxyethyl maleic acid, 2-(meth)acryloyloxyethyl phthalic acid and 2-(meth)acryloyloxyethyl hexahydrophthalic acid.

Other suitable acid group-containing monomers are mentioned in, for example, EP 0 980 682 B1 or EP 0 948 955, which by way of reference are a component part of this application.

Further, phosphoric acid esters with glycerin dimethacrylate or with hydroxyethylmethacrylate or with hydroxypropylmethacrylate can also be used.

The photopolymerizable monomers mentioned can be used individually or in mixtures.

Component (b)—Photoinitiators

Examples of a photoinitiator include catalysts which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019092 A1 or in DE 39 41 629 C2, which by way of reference are a component part of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 A1 or in DE 39 41 629 C2, which by way of reference are a component part of this application.

Further suitable initiators and initiator combinations are described in DE 601 16 142, which by way of reference are a component part of this application.

The photoinitiators that can be used in connection with the present invention are characterized in that through the absorption of light in the wavelength range 300 nm-700 nm, preferably 350 nm-600 nm and particularly preferably 380-500 nm, if necessary in combination with one or more co-initiators, they can bring about the curing of a composition according to the invention.

The absorption maximum of campherquinone (CQ) is approximately 470 nm and thus in the range of blue light. Campherquinone (CQ) is one of the $PI_2$-initiators and is regularly used together with a co-initiator.

A composition according to the invention preferably contains a combination of an alpha-diketone and an aromatic tertiary amine, preferably the combination is of campherquinone (CQ) and ethyl-p-N,N-dimethylaminobenzoate (DABE).

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide. Regarding the structures of suitable phosphine oxides for use in a composition according to the invention, reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a component part of this application.

The phosphine oxides indicated in these printed publications are particularly suitable on their own or in combination with the "alpha-diketone/amine" system as a photopolymerization initiator system in the compositions according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a component part of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a component part of this application.

Component (f)—Initiators for the Chemical Curing

Various initiators for a chemical curing will be known to a person skilled in the art. In this connection reference is made by way of example to EP 1 720 506.

Preferred initiators for chemical curing are benzoyl peroxide (BPO), lauroyl peroxide in particular dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 1495520, WO 02/092021 or in WO 02/092023, which by way of reference are a component part of this application.

Suitable malonyl sulfamides are described in EP 0 059 451 which by way of reference is a component part of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2,6-diocytyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metal such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate), copper acetyl acetonate and copper napththenate.

Component (d)—Polymerization Inhibitors

The dental compositions according to the invention contain one or more inhibitors, also referred to as stabilizers. These are added to a composition in order to prevent spontaneous polymerization. They react with prematurely forming radicals, which are intercepted, prevent premature polymerization and increase the storage stability of the photocurable dental composition. Common inhibitors are phenol derivatives such as hydroquinone monomethylether (HQME) or 2,6-di-tert.butyl-4-methylphenol (BHT). Further inhibitors such as 2,2-diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1, which by way of reference are a component part of this application. Alternative inhibitors are indicated in DE 101 19 831 A1 or in EP 1 563 821 A1, which by way of reference are a component part of this application.

A dental composition according to the invention further comprises (d) one or more polymerization inhibitors to increase the storage stability of the composition, preferably selected from the group consisting of hydroquinone monomethylether (HQME), phenols, here preferably 2,6-di-tert.butyl-4-methyl phenol (BHT) and tert.-butylhydroxy anisol (BHA), 2,2-diphenyl-1-picrylhydrazyl radicals, galvinoxyl radicals, triphenylmethyl radicals, 2,3,6,6,-tetramethylpiperidinyl-1-oxyl radicals (TEMPO) and derivatives thereof and phenothiazine and derivatives thereof.

Molecular weight regulators to be preferably used according to the invention as component (d) of a composition according to the invention are selected from the group consisting of phenols, particularly preferred are 2,6-di-tert.butyl-4-methylphenol (BHT) and tert.-butylhydroxyanisol (BHA).

The polymerization inhibitors of component (d), unlike the molecular weight regulators of component (c), are not capable of H-abstraction in the allyl position.

Where nevertheless in an individual case a polymerization inhibitor can at the same time be considered as a molecular weight regulator for H-abstraction in the allyl position, for the purposes of the present text this will be considered as a molecular weight regulator, in particular for quantitative considerations.

The combination of one or more molecular weight regulators of component (c) and one or more polymerization inhibitors of component (d) in a dual-curing, multi-component dental composition according to the invention leads to a situation, in particular in the embodiments identified as preferred, where after mixing the two or more components, a long extra-oral working of the composition in the mixed state is made possible and after the intra-oral application of the composition in the mixed state, the composition rapidly cures.

The presence of one or more polymerization inhibitors of component (d), preferably of BHT and/or TEMPO, in a dental composition according to the invention, in particular in the abovementioned preferred quantities or quantity ratios, is advantageous because the storage stability of a dental composition according to the invention is significantly increased. Here the relevant effect of the molecular weight regulator(s) (c) is not impaired.

A preferred dental composition according to the invention comprises component (d) in a quantity of 0.005-0.100 wt. %, in particular 0.005-0.075 wt. %, preferably 0.010-0.050 wt. %, in each case in relation to the total mass of the dental composition.

If markedly higher quantities of component (d) are used, then the curing of the dental composition is slowed appreciably.

In further preferred dental compositions according to the invention the ratio of the total mass of component (c) to the total mass of component (d) is in the range 1:5-100:1, preferably in the range 1:1-20:1, more preferably in the range 10:1-20:1, further preferably in the range 11:1-20:1, particularly preferably in the range 12:1-18:1.

In summary, such a combination of component (c) and (d), as well as the effects already set out above, in particular in one of the embodiments identified as preferred, additionally ensures very good storage stability;

during polymerization of the dental composition according to the invention an adjustable/tailored molecular weight distribution following curing, and an acceptable temperature maximum ($T_{max}$) during the polymerization of the dental composition in the oral cavity.

Component (e)—Inorganic Fillers

The inorganic fillers can be used alone or in mixtures. In order to optimize the product features the inorganic fillers can be introduced into the formulations in varying grain sizes. The fillers can have a unimodal or polymodal, for example a bimodal, distribution.

A preferred dental composition according to the invention comprises component (e) in a quantity of at least 10 wt. %, preferably at least 20 wt. %, more preferably at least 25 wt. %, in relation to the total mass of the dental composition.

The total quantity of inorganic fillers in a dental composition according to the invention is preferably at most 95 wt. %, more preferably at most 90 wt. %, further preferably at most 85 wt. % in relation to the total mass of the composition.

The total quantity of inorganic fillers in a dental composition according to the invention is preferably at least 25 wt. %, more preferably at least 30 wt. %, further preferably at least 40 wt. %, in relation to the total mass of the composition.

Compact glasses and various silicic acids in different sizes and states (monodisperse, polydisperse) are used as inorganic fillers.

Suitable inorganic components are for example amorphous materials with a mixed oxide base of $SiO_2$, $ZrO_2$ and/or $TiO_2$, microfine fillers such as pyrogenic silicic acid or precipitated silicic acid and macro- or mini-fillers such as quartz-glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zirconium silicates, hardly soluble metal salts such as barium sulfate or calcium fluoride and X-ray opaque fillers such as ytterbium fluoride.

For a better assembly of the polymer matrix the fillers can be surface modified. One example of surface treatment of the fillers is the use of a silane. Methacryloxypropyltrimethoxysilane is particularly well-suited as a bonding agent.

In order to adjust the rheology dental compositions according to the invention can contain various silicic acids, preferably pyrogenic silicic acids.

In addition materials with a strengthening effect such as glass fibers, polyamide or carbon fibers can be used. The dental composition can also contain fine particle splinters or bead polymerizates, wherein the bead polymerizates can be homo- or copolymers or organically curable monomers.

In a number of compositions according to the invention, preferably no or a comparatively low proportion of organic filler particles are used, since some dental uses require certain, i.e. comparatively high, mechanical properties, which cannot be achieved with organic filler particles.

Where they are present, the total quantity of organic filler particles in a dental composition according to the invention is preferably at most 40 wt. %, more preferably at most 35 wt. %, in relation to the total mass of the composition.

Where a dental composition according to the invention contains organic filler particles, the proportion thereof is preferably in the range 5-35 wt. %, in relation to the total mass of the composition.

A number of preferred dental compositions according to the invention comprise no organic filler particles.

The total quantity of inorganic and organic filler particles in a dental composition according to the invention is preferably at most 95 wt. %, more preferably at most 90 wt. %, further preferably at most 85 wt. %, in relation to the total mass of the composition.

UV absorbers, which for example as a result of their conjugated double bonding systems and aromatic rings are capable of absorbing UV radiation, can if necessary be a component of a dental composition according to the invention. Examples of UV absorbers are 2-hydroxy-4-methoxybenzophenone, salicylic acid phenyl ester or 3-(2'-hydroxy-5'-methylphenyl)-benzotriazole.

Since the teeth are to be rebuilt to look as true to life as possible, it is necessary for the dental compositions according to the invention to be provided in the most varied of color tones. To this end as a rule inorganic colorants and organic pigments are used in very small quantities.

The embodiments of a composition according to the invention identified respectively above as preferred or particularly preferred apply in particular also in combination with other embodiments of a composition according to the invention identified as preferred or particularly preferred.

In accordance with the above remarks, a particularly preferred dual-curing, two-component dental composition according to the invention in the form of two pastes comprises:
(a) one or more photopolymerizable monomers selected from the group of methacrylates;
(b) one or more photoinitiators, selected from the group consisting of alpha-diketones, benzoin alkyl ethers, thioxanthones, benzophenones, acylphosphinoxides, acetophenones, ketals, titanocenes and borates, preferably selected from the group of alpha-diketones, preferably campherquinone;
(c) one or more molecular weight regulators selected from the group consisting of α-terpinene and γ-terpinene;
(d) one or more polymerization inhibitors for increasing the storage stability of the composition, preferably selected from the group consisting of hydroquinone monomethyl ether (HQME), phenols, preferably 2,6-di-tert.-butyl-4-methylphenol (BHT) and tert.-butylhydroxyanisol (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof, preferably from the group of phenols;
(e) one or more inorganic fillers, preferably in a quantity of at least 25 wt. %, in relation to the total weight of the composition;
(f) one or more initiators for a chemical curing at ambient temperature, preferably dibenzoyl peroxide, more preferably dibenzoyl peroxide in combination with N,N-dimethyl-p-toluidine or N,N-dihydroxyethyl-p-toluidine;
wherein the composition contains preferably at most 5 wt. % of alkyl monomethacrylates and/or preferably at most 40 wt. % of organic filler particles.

A further particularly preferred two-component dental composition according to the invention in the form of two pastes comprises:
(a) one or more photopolymerizable monomers selected from the group of methacrylates;
(b) one or more photoinitiators, selected from the group consisting of alpha-diketones, preferably campherquinone, more preferably campherquinone in combination with ethyl-p-N, N-dimethylaminobenzoate;
(c) one or more molecular weight regulators selected from the group consisting of α-terpinene and γ-terpinene;
(d) one or more polymerization inhibitors for increasing the storage stability of the composition, preferably selected from the group consisting of phenols, preferably 2,6-di-tert.-butyl-4-methylphenol (BHT);
(e) one or more inorganic fillers, in a quantity of at least 30 wt. %, preferably in a quantity of at least 40 wt. %, in relation to the total weight of the composition;
(f) one or more initiators for a chemical curing at ambient temperature, preferably dibenzoyl peroxide in combination with N,N-dimethyl-p-toluidine or N,N-dihydroxyethyl-p-toluidine;
wherein the ratio of the total mass of component (c) to the total mass of component (d) is in the range 10:1-20:1, and wherein the composition contains preferably at most 1 wt. % of alkyl monomethacrylates and/or preferably at most 35 wt. % of organic filler particles.

The invention also concerns a dental syringe, preferably a double syringe or a double-chamber cartridge, preferably with a static mixing tube, containing a dental composition according to the invention, preferably in one of the embodiments identified as preferred.

The invention also concerns the use of a compound with two or more double bonds which through abstraction of an allyl H-atom can form a delocalized electron system extending across 5 or more C-atoms of the compound, preferably a diene which through abstraction of an allyl H-atom can form a delocalized electron system extending across 5 C-atoms, preferably selected from the group consisting of α-terpinene and γ-terpinene,
as a molecular weight regulator during the polymerization of monomers selected from the group consisting of acrylates and methacrylates, preferably from the group of methacrylates,
for producing a dual-curing, multi-component dental composition.

The invention likewise concerns a method for producing a dental composition according to the invention, preferably in one of the embodiments identified as preferred or particularly preferred, with the following steps:
production of a multi-component, preferably two-component, system comprising all components (a), (b), (c), (d), (e) and (f), and if necessary further additives,
wherein the initiators of component (f) are distributed over separate components of the dental composition so that a chemical initiation is triggered through the mixing of said components.

The invention further concerns a dental composition according to the invention, preferably in one of the embodiments identified as preferred or particularly preferred, as a dental filling material, as a flowable composite material (flow material), as a crown material, as a bridge material and/or as a stump build-up material.

The invention further concerns a method for treating a dental condition, wherein a dental composition according to the invention, preferably in one of the embodiments indicated as preferred, is used as a dental filling material, as a flowable composite material (flow material), as a crown material, as a bridge material and/or as a stump build-up material. The methods can include any of known methods where such dental compositions may be useful. Such methods include, but are not limited to the methods and uses described herein.

The invention is further explained using the following examples. Unless otherwise indicated all data relate to the weight. The abbreviations common in the trade are used here.

In the following examples the base paste (base) and the catalyst paste (cat.) were mixed in a ratio by weight of 1:1.

Description of the Method for Determining the Temperature Maximum ($T_{max}$)

The heat developed during polymerization was determined using a relative measurement method: a type L (Fe—CuNi) thermal sensor from Reckmann was embedded in a polyethylene holder so that 3 mm of the sensor protruded. This free end of the thermal sensor was positioned centrally in a polyethylene tube of 3 mm internal diameter and 5 mm height. The tube was filled to the brim with material. A colorless, clear acetate film was place over the filled tube so that any excess material was pushed down. In order to trigger the polymerization, a dental LED lamp with a light output of 1,000 mW/cm$^2$ was placed directly on the acetate film and switched on for 10 seconds. The change in voltage of the thermal element as a result of the temperature change was recorded on an L 250-2 xy recorder from Linseis at a sensitivity of 2 mV.

The measurement took place in a climate controlled room at 23° C. and 50% relative humidity under yellow protective light, in order to avoid premature polymerization of the materials. Each individual measurement was only started (lit), once following application of the acetate film a constant temperature had been reached again and the measurement recorder adjusted to the zero line. The maximum deviation of the recorder in scale divisions (0-100 scd) was measured. For the sake of clarity, it is pointed out that while the scale divisions (scd) do correlate to the temperature (i.e. within a series of measurements a higher scale division value corresponds to a higher temperature), they do not numerically correspond to any ° C. values. The measured values indicated are in each case the averages of 3 individual measurements.

Table 1: Exemplary Embodiments with γ-Terpinene
The measurement data are parts by weight

|  |  | Reference | Exp. 1 | Exp. 2 | Exp. 3 | Exp. 4 |
|---|---|---|---|---|---|---|
| Cat. | UDMA | 20.00 | 20.00 | 20.00 | 20.00 | 20.00 |
|  | Ethoxylated bisphenol A dimethacrylate | 40.00 | 40.00 | 40.00 | 40.00 | 40.00 |
|  | BHT | 0.02 | 0.02 | 0.02 | 0.02 | 0.02 |
|  | BPO | 0.25 | 0.25 | 0.25 | 0.25 | 0.25 |
|  | Glass powder | 35.00 | 35.00 | 35.00 | 35.00 | 35.00 |
|  | Aerosil 1 | 2.00 | 2.00 | 2.00 | 2.00 | 2.00 |
|  | Aerosil 2 | 3.50 | 3.50 | 3.50 | 3.50 | 3.50 |
| Base | UDMA | 20.00 | 20.00 | 20.00 | 20.00 | 20.00 |
|  | Ethoxylated bisphenol A dimethacrylate | 40.00 | 40.00 | 40.00 | 40.00 | 40.00 |
|  | N,N-di(hydroxyethyl)-p-toluidine | 2.00 | 2.00 | 2.00 | 2.00 | 2.00 |
|  | Glass powder | 35.00 | 35.00 | 35.00 | 35.00 | 35.00 |
|  | Aerosil 1 | 2.00 | 2.00 | 2.00 | 2.00 | 2.00 |
|  | Aerosil 2 | 3.50 | 3.50 | 3.50 | 3.50 | 3.50 |
|  | Colorants, pigments | 0.50 | 0.50 | 0.50 | 0.50 | 0.50 |
|  | Campherquinone | 0.34 | 0.34 | 0.34 | 0.34 | 0.34 |
|  | DABE | 0.51 | 0.51 | 0.51 | 0.51 | 0.51 |
|  | BHT | 0.02 | 0.02 | 0.02 | 0.02 | 0.02 |
|  | γ-terpinene |  | 0.20 | 0.50 | 1.00 | 2.00 |
|  | $T_{max}$ [scd] | 77 | 66 | 55 | 48 | 42 |

TABLE 1A-1

Conversion of the proportions by weight of BHT and γ-terpinene into weight percentages for the compositions according to Table 1

|  | Reference | Exp. 1 | Exp. 2 | Exp. 3 | Exp. 4 |
|---|---|---|---|---|---|
| BHT (wt. %) | 0.02 | 0.02 | 0.02 | 0.02 | 0.02 |
| γ-terpinene (wt. %) | 0.00 | 0.10 | 0.24 | 0.49 | 0.97 |

The data for "BHT (wt. %)" and "γ-terpinene (wt. %)" in Table 1A-1 are the quantities of BHT or γ-terpinene in weight percent (rounded to two decimal places) in relation to the total weight of the respective composition according to Table 1 after mixing catalyst paste and base paste in the weight ratio 1:1.

TABLE 1A-2

Setting and working times for the compositions according to Table 1

|  | Reference | Exp. 1 | Exp. 2 | Exp. 3 | Exp. 4 |
|---|---|---|---|---|---|
| Working time | 50 sec | 80 sec | 96 sec | 120 sec | 150 sec |
| Setting time | 53 sec | 57 sec | 60 sec | 64 sec | 70 sec |

In accordance with DIN EN ISO 4049 (as specified above), the working times were set at 23° C. and the setting times at 37° C. for the reference example and the examples Exp. 1-Exp. 4 according to Table 1. The respective times are given in Table 1A-2 in seconds.

It can be seen from Table 1A-2 that the setting time deviates increasingly from the working time as the content of γ-terpinene rises. The data provided for working time and setting time are illustrated graphically in FIG. 1—as already explained above.

TABLE 1B

Control compositions not according to the invention, without γ-terpinene with varying content of BHT

|  | BHT (wt. %) | | | | |
|---|---|---|---|---|---|
|  | 0.02 | 0.12 | 0.26 | 0.51 | 0.99 |
| Working time | 50 sec | 65 sec | 81 sec | 96 sec | 118 sec |
| Setting time | 53 sec | 68 sec | 85 sec | 100 sec | 125 sec |

The data for "BHT (wt. %)" in Table 1B are the quantities of BHT in weight percent (rounded to two decimal places), in relation to the total weight of a respective composition, the formulation of which is identical to that of the reference example according to Table 1—after mixing catalyst paste and base paste in the weight ratio 1:1—with the proviso that in each case the quantities of BHT given above in Table 1B were used. The composition of the catalyst paste remained identical to that of the reference example in each case; only the composition of the base paste was varied by changing the BHT proportion.

In accordance with DIN EN ISO 4049 (as specified above), the working times were set at 23° C. and the setting times at 37° C. for these control compositions. The respective times are given in Table 1B in seconds. The data provided for working time and setting time are illustrated graphically in FIG. 2—as already explained above

TABLE 2

Further exemplary embodiments with γ-terpinene

|  |  | Exp. 5 | Exp. 6 | Exp. 7 | Exp. 8 |
|---|---|---|---|---|---|
| Cat. | UDMA | 35.00 | 18.07 | 15.00 | 15.00 |
|  | Ethoxylated bisphenol A dimethacrylate |  | 39.15 |  |  |
|  | Bis-GMA |  |  | 3.00 | 3.00 |
|  | TEDMA | 15.00 |  |  |  |
|  | DODMA |  |  | 6.00 | 6.00 |
|  | HEDMA |  |  | 6.00 | 6.00 |
|  | PEG 300 |  | 0.60 |  |  |
|  | Plasticizer |  | 0.50 |  |  |
|  | BHT | 0.06 | 0.02 | 0.04 | 0.04 |
|  | BPO | 0.50 | 1.51 | 0.70 |  |
|  | 1,3-dimethyl-5-phenyl-barbituric acid sodium salt |  |  |  | 1.20 |
|  | Glass powder | 30.00 | 35.13 | 66.50 | 66.00 |
|  | Pyrogenic silicic acid | 15.00 | 5.02 | 2.76 | 2.76 |
|  | Titanium dioxide | 1.50 |  |  |  |
| Basis | UDMA |  | 18.30 | 14.00 | 14.00 |
|  | Ethoxylated bisphenol A dimethacrylate |  | 37.89 |  |  |
|  | TEDMA | 20.00 |  |  |  |
|  | DODMA |  |  | 6.00 | 6.00 |
|  | HEDMA |  |  | 5.50 | 5.50 |
|  | PEG 300 |  | 0.60 |  |  |
|  | Plasticizer |  | 0.52 |  |  |
|  | Bis-GMA | 35.00 |  | 3.00 | 3.00 |
|  | Glass powder | 27.00 | 35.24 | 67.50 | 67.50 |
|  | Pyrogenic silicic acid | 14.00 | 4.38 | 3.00 | 3.00 |
|  | Titanium dioxide | 1.50 |  |  |  |
|  | Colorants, pigments |  | 0.34 | 0.01 | 0.01 |
|  | Campherquinone | 0.01 | 0.07 | 0.08 | 0.04 |
|  | Cu(II)-acetyl acetonate |  |  |  | 0.25 |
|  | Benzyltributyl ammonium chloride |  |  |  | 0.25 |

TABLE 2-continued

Further exemplary embodiments with γ-terpinene

|  | Exp. 5 | Exp. 6 | Exp. 7 | Exp. 8 |
|---|---|---|---|---|
| DABE |  | 0.10 | 0.11 | 0.1 |
| N,N-Di(hydroxyethyl)-p-toluidine | 0.41 | 2.24 | 0.45 |  |
| γ-terpinene | 0.70 | 0.34 | 0.35 | 0.35 |
| $T_{max}$ [scd] | 48 | 46 | 49 | 43 |

The measurement data are parts by weight

In accordance with DIN EN ISO 4049 (as specified above), the working times were set at 23° C. and the setting times at 37° C. for the examples Exp. 5-Exp. 8. The respective times are given in seconds.

TABLE 3

Working and setting times in examples Exp. 5 - Exp. 8

|  | Exp. 5 | Exp. 6 | Exp. 7 | Exp. 8 |
|---|---|---|---|---|
| Working time | 90 sec | 105 sec | 80 sec | 110 sec |
| Setting time | 57 sec | 62 sec | 57 sec | 64 sec |

The invention claimed is:

1. A dual-curing, multi-component dental composition comprising:
   (a) one or more photopolymerizable monomers selected from the group consisting of acrylates and methacrylates;
   (b) one or more photoinitiators, selected from the group consisting of alpha-diketones, benzoin alkyl ethers, thioxanthones, benzophenones, acylphosphinoxides, acetophenones, ketals, titanocenes, borates and sensitizing colorants;
   (c) one or more molecular weight regulators selected from the group consisting of compounds which can be converted with a radical of a monomer of component (a), wherein the conversion takes place by abstraction of an H-radical from the molecular weight regulator in the allyl position;
   (d) one or more polymerization inhibitors for increasing the storage stability of the composition;
   (e) one or more inorganic fillers;
   (f) one or more initiators for a chemical curing at ambient temperature, and if necessary one or more further additives, wherein: (1) component (c) is present in a quantity of 0.05-5.00 wt. %, in relation to the total mass of the dental composition, (2) component (d) is present in a quantity of 0.005-0.100 wt. %, in relation to the total mass of the dental composition, and/or (3) the ratio of the total mass of component (c) to the total mass of component (d) is in the range of 5:1 to 100:1.

2. The dental composition as claimed in claim 1, wherein said one or more polymerization inhibitors is selected from the group consisting of 2,6-di-tert.-butyl-4-methylphenol (BHT) and tert.-butylhydroxyanisol (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

3. The dental composition as claimed in claim 1, wherein the dental composition comprises two-components.

4. The dental composition as claimed in claim 1, wherein the dental composition comprises two-components, is present in the form of a base paste and a catalyst paste, and wherein the mixing ratios, based on weight, of base paste to catalyst paste are in the range 1:2 to 10:1.

5. The dental composition as claimed in claim 4, wherein component (d) is partially or fully contained in the catalyst paste.

6. The dental composition as claimed in claim 1, wherein component (f) comprises:
   (f-a)
      one or more initiators, selected from the group consisting of inorganic peroxides, organic peroxides, inorganic hydroperoxides, organic hydroperoxides, barbituric acid derivatives, malonyl sulfamides, protonic acids, Lewis or Broensted acids, compounds releasing such acids and carbenium ion donors;
      one or more co-initiators selected from the group consisting of tertiary amines, heavy metal compounds, compounds with ionically bonded halogens or pseudohalogens and weak Broenstedt acids
   and/or
   (f-b) a redox initiator system, comprising
      (f-b1) barbituric acid, thiobarbituric acid, a barbituric acid and/or a thiobarbituric acid derivative,
      (f-b2) if necessary a peroxodisulfate and/or a peroxodiphosphate compound,
      (f-b3) a copper compound,
      (f-b4) a compound with an ionically present halogen atom,
      wherein the initiators of component (f) are distributed over separate components of the dental composition so that a chemical initiation is triggered through the mixing of said components.

7. The dental composition as claimed in claim 6, wherein the catalyst paste contains one or more initiators of component (f-a), and the base paste contains one or more co-initiators of the component (f-a).

8. The dental composition as claimed in claim 1, wherein one or more of the molecular weight regulators of component (c) are compounds with two or more double bonds, preferably compounds with two or more double bonds which through abstraction of an allyl H-atom can form a delocalized electron system, extending across 5 or more C-atoms.

9. The dental composition as claimed in claim 1, wherein one or more molecular weight regulators of component (c), are selected from the group of monoterpenes or from the group consisting of linoleic acid, linolenic acid and other substituted or non-substituted cyclohexadienes.

10. The dental composition as claimed in claim 9, wherein monoterpenes are monoterpene dienes.

11. The dental composition as claimed in claim 9, wherein the monoterpenes are selected from the group consisting of α-terpinene, β-terpinene, γ-terpinene, α-phellandrene, β-phellandrene and terpinolene.

12. The dental composition as claimed in claim 1, comprising
   component (a) in a quantity of 19-70 wt. %;
   component (c) in a quantity of 0.05-5.00 wt. %, and
   component (e) in a quantity of 25-80 wt. %, in each case in relation to the total mass of the dental composition.

13. The dental composition as claimed in claim 1, comprising
   component (a) in a quantity of 19-70 wt. %;
   component (c) in a quantity of 0.05-5.00 wt. %,
   component (e) in a quantity of 25-80 wt. %, and
   components (b) and (f) in a total quantity in the range 0.25-3 wt. %, in each case in relation to the total mass of the dental composition.

14. The dental composition as claimed in claim 1, comprising component (a) in a quantity of 19-70 wt. %;
component (b) in a quantity of 0.05-1.00 wt. %,
component (c) in a quantity of 0.05-5.00 wt. %,
component (e) in a quantity of 25-80 wt. %,
component (f) in a quantity of 0.2-2 wt. %, in each case in relation to the total mass of the dental composition.

15. The dental composition as claimed in claim 1, wherein, as well as one or more photoinitiators of component (b), the composition additionally contains one or more initiators different from component (b) for a chemical curing at ambient temperature of component (f).

16. The dental composition as claimed in claim 1, wherein component (a) contains one of more dimethacrylate monomers selected from the group consisting of ethylene glycol dimethacrylate (EGDMA), 1,6-hexandiol dimethacrylate (HEDMA), triethylene glycol dimethacrylate (TEGDMA), 1,12-dodecandiol-dimethacrylate (DODMA), ethoxylated bisphenol A dimethacrylate, polyethylene glycol dimethacrylate (PEGDMA), 7,7,9-trimethyl-4,13-dioxo-5,12-diazahexadecan-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, glycerin dimethacrylate, bisphenol A glycidyl methacrylate (bis-GMA) and dimethacrylates of dihydroxymethyltricyclo[5.2.1.0$^{2,6}$]decane.

17. The dental composition as claimed in claim 1, wherein the ratio of the total mass of component (c) to the total mass of component (d) is in the range 1:5-100:1.

18. The dental composition as claimed in claim 1, as a dental filling material, as a flowable composite material (flow material), as a crown material, as a bridge material and/or as a stump build-up material.

19. A dental syringe, a double-chamber syringe or a double-chamber cartridge with mixing attachment, containing a dental composition as claimed in claim 1.

20. A method for producing a dental composition as claimed claim 1, with the following steps:
production of a multi-component system comprising all components (a), (b), (c), (d), (e) and (f) and if necessary further additives, wherein the initiators of component (f) are distributed over separate components of the dental composition so that a chemical initiation is triggered through the mixing of said components.

21. A method of producing a dual-curing, multi-component dental composition of claim 1, comprising:
providing a composition comprising monomers selected from the group consisting of acrylates and methacrylates,
combining said composition with a compound with two or more double bonds which through abstraction of an allyl H-atom can form a delocalized electron system extending across 5 or more C-atoms of the compound, and
polymerizing said combination.

22. The dental composition as claimed in claim 1, wherein component (a) is present in a quantity of 30-70 wt. %.

23. The dental composition as claimed in claim 1, wherein said one or more polymerization inhibitors of component (d) are selected from the group consisting of 2,6-di-tert.-butyl-4-methylphenol (BHT) and tert.-butylhydroxyanisol (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof; and
wherein one or more molecular weight regulators of component (c) are selected from the group of monoterpenes or from the group consisting of linoleic acid, linolenic acid and other substituted or non-substituted cyclohexadienes.

* * * * *